United States Patent [19]

Masover et al.

[11] Patent Number: 4,598,045
[45] Date of Patent: Jul. 1, 1986

[54] TRIPHASIC MYCOPLASMATALES DETECTION METHOD

[75] Inventors: Gerald K. Masover, Palo Alto; Milton G. Drysdale, Concord, both of Calif.

[73] Assignee: Hana Biologics, Inc., Berkeley, Calif.

[21] Appl. No.: 703,627

[22] Filed: Feb. 19, 1985

Related U.S. Application Data

[63] Continuation of Ser. No. 411,293, Aug. 25, 1982, abandoned.

[51] Int. Cl.$^4$ .......................... C12Q 1/04; C12N 1/20; C12M 1/24; C12M 1/16
[52] U.S. Cl. .......................... 435/34; 435/32; 435/253; 435/296; 435/299
[58] Field of Search .................. 435/32, 33, 34, 253, 435/296, 299, 870

[56] References Cited

U.S. PATENT DOCUMENTS

| | | | |
|---|---|---|---|
| 2,992,974 | 7/1961 | Belcove et al. | 435/296 X |
| 3,449,210 | 6/1969 | Rohde | 435/296 |
| 3,485,721 | 12/1969 | Woodhour et al. | 435/870 X |
| 3,589,983 | 6/1971 | Holderith et al. | 435/296 |
| 3,651,926 | 3/1972 | Elfast, Jr. | 435/296 X |
| 3,668,075 | 6/1972 | Cekoric, Jr. et al. | 435/34 X |
| 3,838,012 | 9/1974 | Higgens et al. | 435/32 X |
| 3,904,482 | 9/1975 | Mehl | 435/296 X |
| 4,308,347 | 12/1981 | Forrer et al. | 435/296 X |
| 4,387,161 | 6/1983 | McGarrity et al. | 435/870 X |

FOREIGN PATENT DOCUMENTS

| | | | |
|---|---|---|---|
| 560909 | 6/1977 | U.S.S.R. | 435/870 |
| 712441 | 1/1980 | U.S.S.R. | 435/34 |
| 704985 | 1/1980 | U.S.S.R. | 435/34 |

OTHER PUBLICATIONS

Kenny, G. E., Manual of Clinical Microbiology, 3rd ed., American Society of Microbiology, Washington, D.C., 1980, pp. 365-370.
Masover et al., The Prokaryotes, vol. II, Springer-Verlag, N.Y., 1981, pp. 2247-2270.

Primary Examiner—David M. Naff
Attorney, Agent, or Firm—William B. Walker

[57] ABSTRACT

A culture device is disclosed specifically suitable for identifying microorganisms such as Mollicutes comprising a container having opposed transparent optically flat side walls and a nutrient agar medium adhering to the inner surface of a first side wall, and having therein a liquid nutrient medium. During incubation, the nutrient agar medium is spaced apart from the liquid medium with a humid gas phase between the mediums, and the nutrient agar medium can be examined with a microscope through the first wall without opening the container.

11 Claims, 6 Drawing Figures

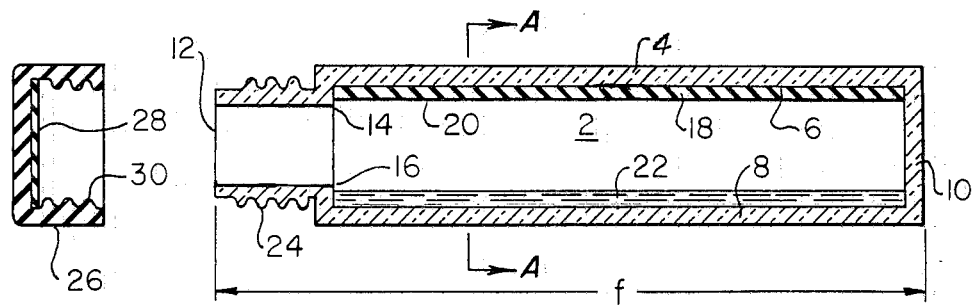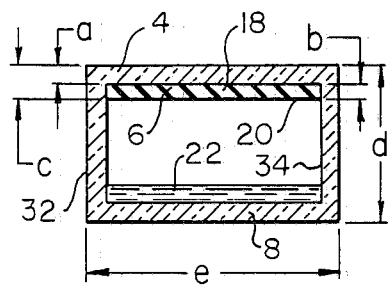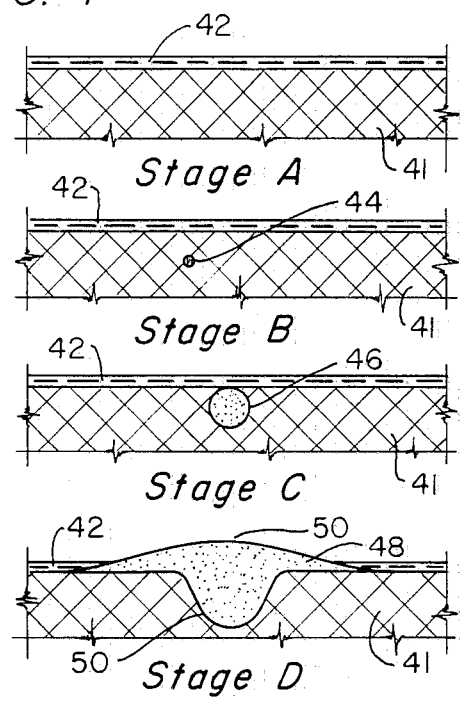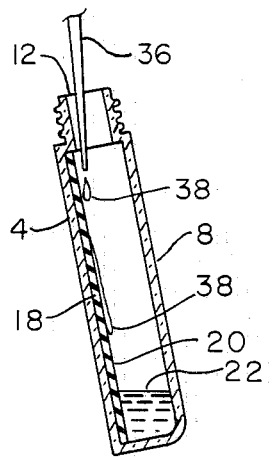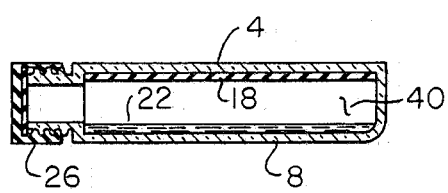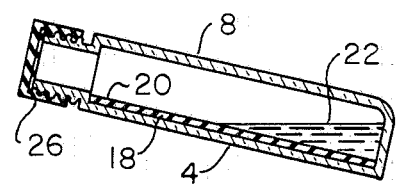

TRIPHASIC MYCOPLASMATALES DETECTION METHOD

RELATIONSHIP TO COPENDING APPLICATION

This application is a continuation of copending application Ser. No. 411,293 filed Aug. 25, 1982, now abandoned.

FIELD OF THE INVENTION

This invention is directed to a device and method for culturing microorganisms for the purpose of identifying them. In particular this invention is directed to a device and method for detecting the presence of Mycoplasmatales with greater convenience and reliability.

BACKGROUND OF THE INVENTION

Description of the Prior Art

A description of media and procedures for identifying certain members of Class Mollicutes is provided by G. Masover and L. Hayflick, "The Genera Mycoplasma, Ureaplasma, and Acholeplasma, and Associated Organisms (Thermoplasmas and Anaeroplasmas), *The Prokaryotes, Vol. II, Springer-Verlag*, New York (1981), the entire contents of which are hereby incorporated by reference.

Sampling, inoculation and incubation procedures and growth medium formulations are also described by G. E. Kenney in the *Manual of Clinical Microbiology*, 3rd edition, American Society of Microbiology, Washington, D.C. (1980), 365-370. A variety of prior art techniques are described. Cultivation in a nutrient broth, and pipette transfer of broth to an agar medium is described. Use of a diphasic medium, that is, an agar layer in the bottom of a test tube covered by a liquid medium is also described. The procedures described in the Manual are representative of the procedures often followed prior to this invention. Three agar plates, a diphasic system and a broth are inoculated with specimen or sample. Each agar plate is incubated under different conditions, one aerobically, another microaerophilically and the third under strict anaerobiosis. The diphasic culture is also incubated under strict anaerobiosis (Kenny, p. 369, supra). Subcultures from the broth to the agar plates and diphasic system are made on the fourth day after incubation of the broth with sample and incubated for an additional 3 to 5 days prior to assessing results. Thus a total of nine cultures are made for a single sample. Despite these complex procedures, the results are often unreliable, even when carried out by a skilled microbiologist due to interlaboratory variations in the microenvironment in which the tests are carried out.

Triphasic systems for blood cultures are described in U.S. Pat. Nos. 2,992,974 and 3,589,983. In the procedures of both patents, simultaneous inoculation of liquid and solid nutrient media with a blood sample is described, and the incubation occurs with the media being separated. U.S. Pat. No. 4,308,347 is directed to a dual container combination wherein a specimen is incubated in a liquid medium in one container and the container is opened, exposing it to the atmosphere, and connected to a second container containing a solid medium. The liquid contents are transferred to the solid medium and incubated in a diphasic mode. The devices disclosed in the above patents are not suitable for carrying out the method of this invention, in particular microscopic examination of the solid media in the unopened device, and the methods described therein are are very different from those of this invention.

U.S. Pat. No. 3,449,210 describes a microorganism culturing assembly which includes a transparent bottle and cap which can be used with solidified culture media. The shape and relative dimensions of the bottle are not suitable for microscopic examination of the contents in accordance with this invention. U.S. Pat. No. 3,651,926 describes a transport system for biological specimens, and U.S. Pat. No. 3,904,482 describes a blood sample cultivation system.

SUMMARY AND OBJECTS OF THE INVENTION

The triphasic Mycoplasmatales culture device of this invention comprises a container having first and second, opposed, transparent sidewalls, an opening and a closure means for sealing the opening. The inner wall surface of the first sidewall is covered with an adherent layer of Mycoplasmatales nutrient agar medium. The container also contains a Mycoplasmatales liquid nutrient medium and sufficient gas to separate the nutrient agar medium from the liquid nutrient medium when the first sidewall is positioned in a horizontal plane above the second sidewall. The distance between the outer surfaces of the first and second sidewalls and the surface quality of the first sidewall permits microscopic examination of the nutrient agar medium through the first sidewall. During use, the nutrient media in the triphasic Mycoplasmatales culture device contains an inhibitory amount of thallium salt and a cell wall inhibiting antibiotic.

The triphasic Mycoplasmatales culture device of this invention prior to adding the liquid nutrient medium comprises a container having first and second, opposed, flat, transparent sidewalls, an opening at one end and a closure means for sealing the opening. The inner wall surface of the first sidewall is covered by an adherent layer of Mycoplasmatales nutrient agar medium, the combined thickness of the agar medium and the first sidewall not exceeding 8 mm. The distance between the outer surfaces of the first and second sidewalls does not exceed 20 mm and the first and second sidewalls have a width of from 22 to 40 mm and a length of from 70 to 85 mm.

A container of this invention for a triphasic Mycoplasmatales culture system comprises first and second, opposed, flat, transparent sidewalls, an opening centrally located at one end and having a diameter less than the distance between the sidewalls. The ends and sidewalls define reservoirs for nutrient media. A closure means is provided for the opening. The distance between the outer surfaces of the first and second sidewalls does not exceed 20 mm, and the first and second sidewalls have a width of 22 to 28 mm and a length of 70 to 85 mm.

A Mycoplasmatales culture inhibitor device of this invention for introducing inhibitors to a Mollicutes culture medium comprises a moisture-free absorbent material impregnated with inhibitory amounts of a thallium salt soluble in Mycoplasmatales nutrient media and a cell wall inhibiting antibiotic. The device is substantially free from moisture.

A method of this invention for detecting Mycoplasmatales in a sample is carried out in the triphasic culture device of this invention described above. The method comprises the following steps:

(a) Inoculating the Mycoplasmatales nutrient agar medium and Mycoplasmatales liquid nutrient medium with sample. Inhibitory quantities of a thallium salt and a cell wall inhibiting antibiotic are introduced to the device, preferably before inoculation. The device is then sealed.

(b) Incubating the device at a temperature of from 35° to 37° C. for at least 48 hours with a gas phase separating the agar and liquid nutrient media (c) Inoculating the Mycoplasmatales nutrient agar medium with the Mycoplasmatales liquid nutrient media in the device without unsealing the opening (d) Reincubating the device at a temperature of from 35° to 37° C. for at least 48 hours with a gas phase separating the agar and liquid nutrient media;

(e) examining the Mycoplasmatales nutrient agar medium through the first sidewall with a microscope without unsealing the opening to detect Mycoplasmatales colonies therein.

Preferably, the Mycoplasmatales nutrient agar medium is separated from the Mycoplasmatales liquid nutrient medium by a gas phase during the microscopic examination.

It is an object of this invention to provide a closed device (biologically contained system) and method for the reliable, accurate, and efficient detection of Mycoplasmatales of the class Mollicutes in biological materials.

It is a further object of this invention to provide a storage stable culture system for detecting Mycoplasmatales which eliminates the need for transporting test specimens and which can be used with standard laboratory equipment.

BRIEF DESCRIPTION OF THE DRAWINGS

FIG. 1 is a cross-sectional view of a triphasic culture device of this invention.

FIG. 2 is a cross-sectional view of the triphasic culture device of this invention taken along the lines A—A in FIG. 1.

FIG. 3 is a cross-sectional view of the triphasic culture device of this invention showing a preferred method for inoculating.

FIG. 4 is a cross-sectional view of the triphasic culture device of this invention in the triphasic position.

FIG. 5 is a cross-sectional view of the triphasic culture device of this invention illustrating the orientation of the device for reinoculation.

FIG. 6 is a cross-sectional view of the typical development of Mycoplasmatales colonies on nutrient agar medium.

DETAILED DESCRIPTION OF THE INVENTION

Microorganism detection and identification continues to be difficult, particularly with small numbers of organisms or with certain organisms which cannot be easily cultured to present a typical colony appearance. Microorganisms of the class Mollicutes, order Mycoplasmatales are perhaps the most difficult to verify because the typical, fully developed colonies are too small for identification with the unaided eye. The device and method of this invention will therefore be described hereinafter with respect to Mycoplasmatales as a representative example but not by way of limitation. The device and method is widely applicable, particularly when relatively small populations of microorganisms are present in biological material to be tested.

Microorganisms known generally by the trivial name "mycoplasmas" have unique properties. The single biological property that most distinguishes these microorganisms from all others is that they lack the cell wall present in all bacteria and are also the smallest known organisms capable of reproduction in axenic (lifeless) culture media. The absence of a cell wall is reflected in the name given to the class; Mollicutes (soft skin). They are incapable of synthesizing cell wall precursors such as muramic and diaminopimelic acids. Their small size (lower size limit, approximately 0.33 micron diameter sphere) is characterized by their ability to pass through a 450-nm (and often a 220-nm) membrane filter. This is probably the chief reason why the agar colonies produced by them are typically small (0.1–0.6 mm). Due to their small size and lack of a rigid cell wall, the organisms are able to penetrate and grow in the interstices of agar fibrils to produce a characteristic colony with an appearance often likened to a "fried egg". The organisms' exact mode of replication is not clear. The fundamental act of replication in these, as in other prokaryotes, is replication of a single circular DNA molecule. The process by which daughter DNA molecules are separated into daughter cells is the aspect of division that is unclear. If the DNA replication is followed by equal division of the cytoplasm, then binary fission occurs. If, however, the cytoplasm is unequally divided after DNA replication, the process is called budding. Both processes have been described. Both motile and nonmotile forms are known.

Many Mycoplasma species produce diseases in domestic animals that are of significant worldwide economic importance. The only Mycoplasma species proven to cause a human disease (*Mycoplasma pneumoniae*) is the etiological agent of a significant portion of the pneumonic conditions that affect man. Its implication in a myriad of medically important sequelae is strongly suspected. Recently, good evidence for a role of Ureaplasma in human pathogenicity has been published. In recent years, organisms of the genus Spiroplasma have been implicated in economically important plant diseases.

In addition to the diseases caused by Mycoplasma species, a major incentive for understanding more about mycoplasma biology comes from the field of cell culture. To the tissue culturist, mycoplasmas are a major nuisance. Their presence in cell cultures often goes unrecognized and they can seriously confound the interpretation of experimental results. Their source is often unknown and they can only rarely be eliminated. About 10% of all cell cultures in use today are probably contaminated with Mollicutes.

Mycoplasmatales found in cell cultures are predominantly *Acholeplasma laidlawii*, *Mycoplasma arginini*, *Mycoplasma orale*, and *Mycoplasma hyorhinis*. The first two are associated with cattle and are usually introduced into cell cultures with the bovine serum used almost universally by cell culturists. *M. orale* is found in the human oral cavity and is probably introduced by poor aseptic technique or from other contaminated cell cultures. *M. hyorhinis* is associated with swine and although it is unproven, the origin of this contaminant is thought to be the crude porcine pancreatic extract, commonly called typsin, which is widely used in cell culture techniques. The only Mycoplasmatales that have been found to contaminate cell cultures are Mycoplasma and Acholeplasma species. The human pathogen *M. pneumoniae* has never been found as a cell culture contaminant. It is ordinarily found in the respiratory tract of persons experiencing, or recovering from primary atypical pneumonia. Ureaplasma spp. which are found in the urogenital tract of humans and animals are rarely if ever found as cell culture contaminants, with the possible exception of amniotic fluid cultures now regularly used for genetic counseling (cytogenetics).

Mycoplasmatales contamination of culture media used in fermentation and in particular mammalian cell culture media has frequently gone undetected for prolonged periods of time because of the difficulty of verifying its presence. Many species of Mycoplasma are present in the natural flora of humans and others are present on account of infections and disease. As a result, culture media being manipulated in an open environment is continuously exposed to contamination, particularly by *M. orale* (from lack of aseptic procedures for sampling, inoculation and examination).

Furthermore, the prior art procedures for culturing Mycoplasmatales are deficient in many aspects. The microorganism requires that the agar nutrient medium remain fully saturated with liquid and that no dehydration of the agar surface be permitted before or during incubation. The common Petri dishes and other conventional culture devices used with Mycoplasmatales are not designed to maintain the integrity of the agar growth surface for the extended times often necessary for colony formation.

The liquid phase in diphasic systems interferes with typical colony growth development on the agar medium. The triphasic system of the invention permits a single simultaneous inoculation of liquid and agar media and thereafter, allows initial incubation, reinoculation, a second incubation and examination in a totally closed system and humid system. It achieves agar surface integrity without interfering with development of a typical colony structure in the agar. It also minimizes risk of extraneous contamination.

Referring to FIG. 1, a cross-sectional view of the triphasic culture device of this invention is shown. This device comprises a container 2 having a flat, transparent sidewall 4 with an inner surface 6. The container has a second, flat, transparent opposed sidewall 8 and an end 10 and an opening 12 opposite the end 10. The inner diameter of the opening 12 is smaller than the distance between the inner surfaces of the sidewalls 4 and 8, defining shoulders 14 and 16. The shoulders 14 and 16 in conjunction with the sidewalls 4 and 8 and the end 10 provide reservoirs for nutrient media. The Mycoplasmatales nutrient agar media 18 constitutes a layer adhering to the inner surface 6 of the sidewall 4.

When the sidewall 4 is in a position above the liquid medium 22 as shown in FIG. 1, the volume of liquid nutrient medium 22 should not exceed the capacity of the reservoir formed by the shoulder 16 and the combined volume of the nutrient medium 18 and 22 should not exceed 50 percent of the volume capacity of the container 2. In the position shown in FIG. 1, a gas-filled volume constitutes the third phase of the triphasic system. The surface of the liquid nutrient medium 22 is spaced apart from the opposed surface 20 of the nutrient agar medium 18 so that the liquid nutrient medium 22 and the agar medium 18 do not contact. The space between the liquid nutrient medium 22 and the nutrient agar medium 18 is filled with gas. The integrity of the nutrient agar medium is maintained by the constant saturated humidity derived from the liquid nutrient media in the closed system.

The cap 26 is of standard construction with a sealing layer 28 and threads 30 designed to engage threads 24 of the container opening 12.

Referring to FIG. 2, a cross-sectional view of the culture device of FIG. 1, taken along the lines A—A is shown. In addition to the components previously described, this view shows sidewalls 32 and 34 which, in conjunction with the sidewalls 4 and 8 and the end 10 form the container.

The sidewall 4 preferably has a thickness a of from 1 to 1.5 mm. and the nutrient agar media preferably has a thickness b of from 2.5 to 3.5 mm. The combined thickness c of the sidewall 4 and nutrient agar media 18 should not exceed 8 mm and is preferably not more than 5 mm. The thickness d (the distance between the exterior surfaces of the sidewalls 4 and 8) should not exceed 20 mm. Greater thicknesses cannot be accommodated with most laboratory microscopes. The sidewalls 4 and 8 preferably have widths e of from 22 to 40 mm (optionally from 22 to 27 mm) and lengths f (see FIG. 1) of from 70 to 85 mm. The exterior surfaces of the container preferably come together at 90° and angles, and the edges and corners are preferably not curved so that the container can be securely and easily positioned for microscopic examination.

The container 2 is made of solid transparent material which can be either plastic or glass. Preferably it is constructed of a plastic which will retain surfaces through which light can be focused and the agar nutrient medium can be viewed without significant distortion. The container can be made by conventional procedures by injection or blow-molding techniques. Alternatively, the sidewall 4 can be separately formed by casting, calendaring or injection molding procedures to provide a plate with flat surfaces having the optical qualities necessary for microscopic viewing. The plate can then be attached and sealed to the other components by ultrasonic, chemical or solvent bonding to provide a water and air-tight container.

The cap 26 and the sealing layer 28 can be of any conventional construction which will provide an airtight seal when engaging the bottle.

The Mycoplasmatales nutrient media for both solid and liquid phases in the triphasic device of this system can be selected from those previously developed. Examples of suitable compositions are described in the *Manual of Clinical Microbiology*, supra. A particularly comprehensive list of Mycoplasmatales reagent formulations is provided in *NIAID Catalog of Research Reagents* by S. Cunningham, Research Resources Branch, National Institute of Allergy and Infectious Diseases, National Institutes of Health, Bethesda, Md., the entire contents of which are hereby incorporated by reference.

Inhibition of the growth of organisms other than Mycoplasmatales is achieved by providing inhibiting concentrations of one or more thallium compounds and one or more cell wall inhibiting antibiotics in the nutrient media. Suitable thallium compounds are salts, esters or other forms which are soluble in the nutrient media in inhibitory concentrations and can be thallium acetate, thallium propionate and the like. Suitable cell wall inhibiting antibiotics include one or more penicillins, cephalosporins, ampicillin and the like. Thallous acetate concentrations of 0.05 weight percent and penicillin G concentrations of 1000 units per ml., for example, are inhibitory.

Since the members of the class Mollicutes are without a bacterial cell wall, they are unaffected by those antibodies which interfere with bacterial cell wall biosynthesis. The penicillins are common examples of such antibiotics. In addition, Mollicutes (except Ureaplasma spp.) are insensitive to the heavy metal thallium. These properties are used to advantage in selection of Mollicutes from mixed microbial populations. Thus, most media formulations used to select for mycoplasmas contain penicillin (100 to 1000 units per ml) and thallous acetate (1:1000 to 1:4000). Because penicillin in solution has a very short half-life, prepared media containing penicillin loses its selective capability quickly (ca. 14 days).

An integral part of this invention is the preparation filter paper disks or strips saturated with penicillin and thallous acetate or, for Ureaplasma spp., penicillin and Nystatin such that the antibacterial content of the disk gives an appropriate bacteriocidal concentration in both the liquid and agar phases of the triphasic monochamber.

In use, the appropriate dry disk is added to the flask aseptically, and the flask is closed. A few moments are allowed for the antibiotic to become distributed in the liquid medium and then in the agar portion. This is accomplished in a single step by placing the flask agar side down with the liquid and the disk on top of and in contact with the agar.

The sample is then added, and one may expect that bacteria other than Mollicutes in the sample will be inhibited or killed leaving only Mollicutes to multiply in the growth chamber. An important advantage of adding the antibiotic in this fashion is that the penicillin which is labile in solution is kept dry until the moment of use, thus assuring antibiotic potency and extending the useful shelf life of the system very considerably.

In addition, clinical samples containing a variety of microorganisms may be tested for Mollicutes in this system by using the appropriate selective antibiotic discs and medium formulations.

The nutrient media also preferably contain a pH indicating dye such as phenol Red or the like. The pH media pH is sensitive to microbial metabolic activity, and in the growth of Mycoplasmatales, may be the first positive visual indication of the presence of the microorganism. The purpose of phenol red, a pH indicator dye, is to provide a color change in response to pH changes which, in turn, occur as a result of microbial metabolism. Organisms which metabolize glucose to acids cause the media, which is cherry red at pH 7.5, to become orange or yellow (more acid). Organisms which metabolize arginine with concomitant production of ammonia (alkaline), cause the color to change to a deep purple-red. These two reactions are very common among Mycoplasmatales. A similar formulation in which the arginine and glucose are omitted and urea (0.1% w/v) is added, is used at a starting pH of 6.0 to 6.3 (yellow with phenol red). Hydrolysis of the urea, accomplished only by Ureaplasma spp. among the Mollicutes, produces ammonia and an alkaline (red) pH change. Urea hydrolysis in the absence of added arginine and glucose substrates produces a red color. Color change of the medium and the absence of turbidity of the broth are therefore diagnostic aids for Ureaplasma spp.

The nutrient compositions of the liquid and agar phases can initially be the same or different, it being recognized that natural diffusion tends to yield a uniform nutrient composition in any event. In preparing the nutrient agar medium layer in the device of this invention, the heated, liquified nutrient mixture is introduced into the container 2 with the side 4 in a position below side 8. Cooling yields gelatinization. The liquid nutrient is then introduced into the container.

The method of this invention is generally described with respect to an evaluation of a sample for the presence of Mycoplasmatales. The various stages are illustrated in FIGS. 3-5.

FIG. 3 illustrates the initial inoculation. An inhibiting amount of a thallium salt and a cell wall inhibiting antibiotic are preferably introduced before inoculation with the sample or specimen. The triphasic device of this invention is held in a slightly tilted position, and the pipette 36 is inserted into the container to the extent necessary to direct the sample droplets 38 to the center of the agar surface 20, the sample leaving a track down the center of the agar surface to the liquid medium 22.

The cap is placed on the device in sealing engagement, and the device is then carefully reoriented to the position shown in FIG. 4 without disturbing the initial incubation track on the solid agar surface 20. The gas phase 40 separates the nutrient agar medium 18 from the liquid phase 22. This gas phase is saturated with moisture as a result of the closed triphasic nature of this system, and the agar surface is therefore protected from dehydration. The initial incubation is preferably carried out (for Mycoplasmatales) at from 35° to 37° C. for at least 48 hours and preferably for from 72 to 120 hours. The incubation time can be reduced if a color indicator change indicates major metabolic microbial activity.

The incubation track and the liquid phase can then be examined visually with and without microscopic examination for change of medium color due to pH indicator and for development of typical colonies on the agar medium. Reinoculation is then effected. For reinoculation, the culture device is carefully oriented to a vertical position and then is tilted to the position shown in FIG. 5 to contact the surface 20 with the liquid phase 22. Any Mycoplasmatales initially present will have multiplied. Preferably liquid phase 22 contacts less than the entire surface 20 of the nutrient agar layer 18. For example, as shown in FIG. 5 approximately 50 percent of the surface of the agar plate 18 is contacted by the liquid phase 22. The bottle is then oriented to a vertical position and then carefully returned to the position shown in FIG. 4 without increasing contact between the liquid phase and the nutrient agar surface.

After further incubation at from 35° to 37° C. for at least 24 hours and preferably for from 72 to 120 hours, the incubation device is inspected to identify the microorganism. The contents, both liquid and agar media can be examined by conventional procedures to identify the colony size and growth habits in both media. For Mycoplasmatales, however, the mature colonies are too small to be visually examined by the unaided eye, and microscopic examination is necessary.

With the device of invention, this microscopic examination can be carried out without breaking the seal. The device in the orientation shown in FIG. 4 can be placed in the view field of a standard microscope, and the microscope focused on the field within the nutrient agar medium 18 through the sidewall 4. The light source can be also focused for the visual plane in the nutrient agar layer 18, the light coming through the transparent sidewall 8.

Because of their small size, relatively high titers (numbers) of Mycoplasmatales (i.e., $10^7$ to $10^8$/ml) do not cause substantial turbidity. Thus the lower (liquid) phase does not interfere with light transmission from the light source during microscopic examination.

Obviously for microscopic examination through the sidewall 4, the surfaces thereof must flat and free from imperfections which would distort the image. Optical quality microscope slides is desirable.

Mollicutes colonies on agar medium are usually from 0.6 to 0.1 mm in diameter. Ureaplasma colonies are more often 0.01 mm to 0.03 mm in diameter, although larger colonies are possible under some conditions. Mollicutes grow up from within the intersticies of the agar medium, and together with a peripheral surface growth, produce a central nipple in most colonies which, when viewed through the microscope, gives to them their characteristic "fried egg" appearance. However, this property is not characteristic of all mycoplasma isolates and is strongly influenced by several environmental conditions. This invention minimizes change in the environmental conditions within the growth chamber. The agar gel strength, a critical environmental factor, can be optimized and maintained throughout incubation.

FIG. 6 shows the stages of typical colony development of Mycoplasmatales on nutrient agar in vertical cross-section. Stage A shows the agar before inoculation, 40 being a free film of nutrient solution phase and 41 being the nutrient agar phase. Stage B after inoculation shows the typical migration of a single microorganism 44 below the agar surface. Stage C shows an intermediate colony 46 as it grows with individual organisms and agar fibrils intertwined to form a spherical mass approaching the agar surface after approximately 24 hours from inoculation. Approximately 24–48 hours after inoculation, the colony growth spreads into the aqueous surface film 40 forming a peripheral zone 48 and a slightly raised central zone 50 which gives the appearance of a "fried egg" when viewed from top or bottom, the axis of viewing being perpendicular to the plane of the agar growth surface.

Mycoplasma colonies are often confused with several kinds of artifacts including "pseudocolonies" that are composed of magnesium and calcium soap crystals, water droplets, bubbles, and animal cells. This invention minimizes formation of many such artifacts by maintaining a constant internal milieu in the closed growth chamber.

This invention is further illustrated by the following specific but non-limiting examples. Temperatures are given in degrees Centigrade.

PREPARATION 1

The following ingredients are combined to form a broth:

| Component | Amount | |
|---|---|---|
| Heat activated Horse Serum | 10% v/v | 100 ml |
| Fresh yeast extract | 10% v/v | 100 ml |
| Glucose | 0.5% w/v | 5 g |
| Arginine HCl | 0.5% w/v | 5 g |
| Potassium Phosphate Buffer pH 7.5 | 50 mM | 4.75 g[a] |
| Phenol Red | 0.005% w/v | .05 g |
| PPLO Broth without Crystal Violet | 2.1% w/v | 21 g |
| Deionized Water sufficient to make | | 1000 ml |
| (final pH of 7.5 ± 0.15) | | |

[a]Calculated as PO$_4$

Heat inactivation of the horse serum means subjecting the serum to 56° C. temperature for 30 to 60 minutes. This procedure destroys a heat labile serum component of the group of biomolecules collectively called complement. In the presence of specific antibody to a mycoplasma, the complement affixes to the antibody-organism complex and lyses the microorganism. Heat inactivation is a precaution to prevent this phenomenon of complement dependant killing of the cells being grown on the specific medium formulations given above.

Since serum is rich in protein which is denatured and thereby rendered insoluble at 60° C., it is added aseptically in sterile form to the media being held between 48° C. and 58° C. in a water bath. The temperature cannot reasonably be allowed to be less than 48° C. because the agar gels at 44° C. to 45° C. and once gelled will not dissolve again until a temperature of 100° C. is reached. Thus, the temperature limits for serum addition are critical to preparation of the agar phase of the medium. The broth may be cooled to any temperature below 59° C. (but above freezing) without effect to the medium composition although, in practice, a better triphasic preparation results by keeping both medium formulations at the same temperature during manufacture of the triphasic monochamber.

PREPARATION 2

Agar

To the broth of Preparation 1 is added agar sufficient to make a final concentration of 1.3% to 1.5% w/v.

PREPARATION 3

Fresh Yeast Extract 250 grams of active dry Bakers' yeast is added to 1 liter of distilled water and heated with stirring until boiling begins. Slow boiling is continued for 15 minutes. The mixture is allowed to cool and is centrifuged at 8,000 to 10,000 × g for 20 to 30 minutes. The clear supernatant fluid is the yeast extract and is poured off the sedimented yeast solids. Sufficient 1N NaOH is added to give pH 7.5; the yeast extract is then placed in appropriate sized screw-capped bottles and autoclaved at 121° C. for 15 minutes. When cool, the caps are tightened, proper labels are affixed to each bottle, and the bottles are stored at −20° C. or lower. At this temperature, the extract is stable for at least 6 months.

PREPARATION 4

Inhibitor Disks

Absorbent paper disks (¼ in, Analytical Paper No. 740-E, S&S, Co.) are saturated with a solution of 0.9 g thallous acetate and 100 mg Penicillin G in 11 ml of absolute ethanol. Each disk holds approximately 10 μl of solution. Excess liquid is removed and the disks dried.

Each disk provides sufficient inhibitor to provide to 6 ml of nutrient media, a concentration of 1000 units/ml Penicillin G and 0.05 wt.% thallous acetate.

The above procedure is carried out under sterile conditions using sterile disks, solvents, and inhibitors.

EXAMPLE

Step 1

Remove the flasks from the refrigerator where they are being stored. Each set of tests should include at least one flask as an uninoculated negative control for color change comparisons. If the object is to determine whether or not the cell culture or medium/medium-component has a procaryotic contaminant, it is not necessary to use antibiotic disks. However, if determination of the nature and source of a contaminant is desired, a flask with an antibiotic disk and a flask without the antibiotic should be used for each test. One antibiotic disk (penicillin and thallous acetate) is aseptically added to each flask and allowed to release its antibiotic during a period of about 5 minutes during which the flask containing a disk is recapped and placed *agar side down* (broth covering agar) on the work surface—preferably in a laminar flow hood.

Step 2

Hold the flask upright, loosen, or under asceptic conditions, remove the cap and allow liquid medium drainage from the surface for 2 to 5 minutes. Introduce 0.2 to 1.0 ml of sample using a 1.0 ml or a Pasteur pipet. The sample is allowed to 'dribble' down the center portion of the agar surface and into the broth. When withdrawing the pipet, stab or slash the agar surface near the top of the flask. This is important to help identify the agar surface during microscopic examination. Ideally, the flasks should be allowed to stand upright with the cap loose or off, if in a laminar flow hood, for about 2 to 5 minutes. This allows the inoculum to penetrate into the agar phase and is important for formation of classical 'fried egg' mycoplasma colonies.

From this point on the orientation of the flask is critical to optimal results.

Step 3

Close the flask tightly to avoid leakage, and incubate at 35° to 37° C., broth side down. Contact between the agar and broth is avoided.

Step 4

Continue incubation until a color change is seen or for 3 to 5 days. The flask may be removed from the incubator periodically for microscopic examination if desired. However, maintain agar side up and avoid splashing the broth phase onto the agar.

Step 5

Microscopic Examination:

Mycoplasma colonies are readily visualized at 40× to 100× total magnification. The thin agar layer and optical quality and thickness of the plastic of the flask permit easy observation using lower power objective lenses (4×, 10×, 16×) which have adequate working distance to focus through the agar. A conventional upright microscope or a good dissecting microscope are best used in order to avoid covering the agar growth surface with the broth as would be required using an inverted microscope. Covering the agar growth surface with the broth phase will not interfere with observation of mycoplasma colonies but will reinoculate the agar which is not desirable until several days after the original inoculation. The proper plane of focus on can be easily found by using the hole or scratch which was previously made on the agar (step 2). In addition, if the flask has been properly inoculated, the "edge of the inoculation" can be identified and compared to an uninoculated adjacent area (step 2). Mycoplasma colonies should be distinguished from pseudo-colonies of cells, debris, bits of agar, etc. Conventional light microscopy is generally easier to use for discerning mycoplasma colonies although phase-contrast microscopy is effective also.

If no mycoplasma colonies and no color change (acid or alkaline) are observed after 5 days, reinoculate the agar surface as follows:

(a) Remove the flask from the incubator.

(b) Hold it upright (cap up).

(c) Tilt it gently so that the broth washes over about half the agar surface—again leaving an "edge of inoculum" as a marker (this time the "edge" is perpendicular to the long axis of the flask and the first inoculum (see diagram).

(d) Carefully reorient the flask to its original broth-down position.

(e) Place in the incubator for another 3 to 5 days.

Step 6

Most (not all) of the mycoplasmas which infect tissue cultures will cause an acid (*A. laidlawii*) or alkaline (*M. arginini, M. hominis*) color change in the medium—both agar and broth. *A. laidlawii* may even cause turbidity. This is the most common contaminant.

Heavy initial contamination ($10^5$–$10^7$/ml supernatant medium) will become apparent in as little as 48 hours (sometimes less). This, however, depends on the strain present and could take the full 3 to 5 days to become apparent.

Very low initial numbers of mycoplasmas ($10^1$ to $10^2$/ml) are easily missed as a result of sampling errors in a poisson distributed particle (the mycoplasma) in the culture medium. Thus, a larger (1.0 ml) sample is preferable to increase chances of picking up one of a few mycoplasmas or bacteria, yeasts, etc. that might be in a tissue culture. In such cases, no colonies or perhaps very few are seen on the agar after the first inoculation of the agar. However, large numbers will be seen after the second inoculation of the agar (step 5).

The invention claimed is:

1. A method for detecting Mycoplasmatales in a sample with a triphasic culture device comprising a container having first and second, opposed, transparent sidewalls, an opening and a closure means for sealing the opening, the inner wall surface of the first sidewall being covered with an adherent layer of Mycoplasmatales nutrient agar medium, the container also containing a Mycoplasmatales liquid nutrient medium and a gas phase, the nutrient agar medium being spaced apart from the liquid nutrient medium with the gas phase in between the mediums when the first sidewall is positioned in a horizontal plane above the second sidewall, the distance between the outer surfaces of the first and second sidewalls and the surface quality of the first sidewall permitting microscopic examination of the nutrient medium through the first sidewall, said method comprising (a) introducing inhibitory quantities of a thallium salt and a cell-wall inhibiting antibiotic through the opening in the container, inoculating the Mycoplasmatales nutrient agar medium and the Mycoplasmatales liquid nutrient medium with a sample, and closing the opening to seal the container;

(b) incubating the container at a temperature of from 35° to 37° C. for at least 48 hours with the container oriented to maintain the nutrient agar medium spaced apart from the liquid nutrient medium with the gas phase between the mediums;

(c) inoculating the Mycoplasmatales nutrient agar medium with the Mycoplasmatales liquid nutrient medium in the container without unsealing the container;

(d) reincubating the container at a temperature of from 35° to 37° C. for at least 48 hours with the container oriented to maintain the nutrient agar medium spaced apart from the liquid nutrient medium with the gas phase between the mediums; and (e) examining the Mycoplasmatales nutrient agar medium through the first sidewall with a microscope without unsealing the container to detect Mycoplasmatales colonies therein.

2. The method of claim 1 wherein the Mycoplasmatales nutrient agar medium is spaced apart from the Mycoplasmatales liquid nutrient medium during the microscopic examination.

3. The method of claim 1 wherein the nutrient mediums contain a pH indicator dye, and after incubation, the nutrient mediums are examined for color change indicating microbial metabolic activity.

4. The method of claim 3 wherein the nutrient mediums are examined after each incubation for color change indicating microbial activity.

5. The method for detecting Mycoplasmatales of claim 1 wherein the first and second sidewalls of the culture device are flat and the combined thickness of the nutrient agar medium and first sidewall does not exceed 8 mm.

6. The method for detecting Mycolasmatales of claim 1 wherein the gas has a volume of at least 50 percent of the container volume.

7. The method for detecting Mycoplasmatales of claim 5 wherein the distance between the outer surfaces of the first and second sidewalls does not exceed 20 mm.

8. The method of detecting Mycoplasmatales of claim 5 wherein the distances between the outer surfaces of the first and second sidewalls is from 22 to 40 mm and the lengths of the sidewalls are from 70 to 85 mm.

9. The method for detecting Mycoplasmatales of claim 1 wherein a nutrient medium contains a pH indicator dye.

10. The method for detecting Mycoplasmatales of claim 1 wherein the combined thickness of the agar medium and the first sidewall does not exceed 8 mm, the distance between the outer surfaces of the first and second sidewalls is from 22 to 40 mm and the lengths of the sidewalls are from 70 to 85 mm.

11. The method for detecting Mycoplasmatales of claim 10 wherein the combined thickness of the agar medium and the first sidewall does not exceed 5 mm and the first and second sidewalls have a distance between the outer surfaces of from 22 to 28 mm.

* * * * *